United States Patent
Brockway et al.

(10) Patent No.: US 7,425,200 B2
(45) Date of Patent: *Sep. 16, 2008

(54) IMPLANTABLE SENSOR WITH WIRELESS COMMUNICATION

(75) Inventors: Brian P. Brockway, Shoreview, MN (US); Perry Alton Mills, Arden Hills, MN (US); Lynn M. Zwiers, Lino Lakes, MI (US)

(73) Assignee: Transoma Medical, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/146,555

(22) Filed: May 15, 2002

(65) Prior Publication Data

US 2002/0138009 A1  Sep. 26, 2002

Related U.S. Application Data

(62) Division of application No. 09/159,653, filed on Sep. 24, 1998, now Pat. No. 6,409,674.

(51) Int. Cl.
*A61B 5/00* (2006.01)

(52) U.S. Cl. .................... 600/486; 600/485

(58) Field of Classification Search .......... 600/485, 600/450, 493–6, 486, 488, 561
See application file for complete search history.

(56) References Cited

U.S. PATENT DOCUMENTS 3,867,950 A  2/1975  Fischell
3,942,382 A  3/1976  Hok
4,207,903 A  6/1980  O'Neill
RE30,366 E  8/1980  Rasor et al.

(Continued)

FOREIGN PATENT DOCUMENTS

DE  19644856 A1  5/1997

(Continued)

OTHER PUBLICATIONS

"Medtronic Announces Two Major Milestones in its Effort to Treat Patients with Heart Failure", Medtronic Press Release (2 pages), (Aug. 18, 1998).

(Continued)

*Primary Examiner*—Robert L Nasser
(74) *Attorney, Agent, or Firm*—Fish & Richardson P.C.

(57) ABSTRACT

An implantable sensor device, such as a pressure monitor, is implanted in the left ventricle (LV), in other heart chambers, or elsewhere, from which it wirelessly communicates pressure information to a remote communication device. The sensor device can be implanted using a placement catheter, an endoscope, or a laparoscope. The device can be secured entirely within the LV or heart wall, such as by using a corkscrew, a helical anchor, a harpoon, a threaded member, a hook, a barb, a fastener, a suture, or a mesh or coating for receiving fibrous tissue growth. The implantable sensor device provides less invasive chronic measurements of left ventricular blood pressure or other physical parameters. The wireless communication techniques include radio-telemetry, inductive coupling, passive transponders, and using the body as a conductor (referred to as "intracorporeal conductive communication" or a "personal area network"). Data from the receiver is downloadable into a computer for analysis or display.

19 Claims, 8 Drawing Sheets

U.S. PATENT DOCUMENTS

| | | | |
|---|---|---|---|
| 4,494,950 A | | 1/1985 | Fischell |
| 4,596,563 A | | 6/1986 | Pande |
| 4,718,425 A | | 1/1988 | Tanaka et al. |
| 4,796,641 A | | 1/1989 | Mills et al. |
| 4,846,191 A | * | 7/1989 | Brockway et al. ............ 600/561 |
| 4,899,752 A | | 2/1990 | Cohen |
| 4,913,147 A | | 4/1990 | Fahlstrom et al. |
| 4,934,369 A | | 6/1990 | Maxwell |
| 4,987,897 A | | 1/1991 | Funke |
| 5,129,394 A | | 7/1992 | Mehra |
| 5,192,314 A | | 3/1993 | Daskalakis |
| 5,353,800 A | * | 10/1994 | Pohndorf et al. ............ 600/486 |
| 5,373,852 A | | 12/1994 | Harrison et al. |
| 5,374,287 A | * | 12/1994 | Rubin ........................ 607/131 |
| 5,411,551 A | | 5/1995 | Winston et al. |
| 5,431,171 A | | 7/1995 | Harrison et al. |
| 5,487,760 A | | 1/1996 | Villafana |
| 5,535,752 A | | 7/1996 | Halperin et al. |
| 5,538,005 A | | 7/1996 | Harrison et al. |
| 5,551,427 A | * | 9/1996 | Altman ........................ 600/374 |
| 5,562,726 A | * | 10/1996 | Chuter ........................ 623/1.35 |
| 5,593,430 A | | 1/1997 | Renger |
| 5,702,427 A | | 12/1997 | Ecker et al. |
| 5,796,827 A | | 8/1998 | Coppersmith et al. |
| 5,807,265 A | | 9/1998 | Itoigawa et al. |
| 5,836,886 A | | 11/1998 | Itoigawa et al. |
| 5,860,938 A | | 1/1999 | Lafontaine et al. |
| 5,899,927 A | | 5/1999 | Ecker et al. |
| 5,906,573 A | * | 5/1999 | Aretz ............................. 600/3 |
| 5,911,704 A | * | 6/1999 | Humes .................... 604/93.01 |
| 5,967,986 A | * | 10/1999 | Cimochowski et al. ..... 600/454 |
| 6,015,386 A | | 1/2000 | Kensey et al. |
| 6,015,387 A | | 1/2000 | Schwartz et al. |
| 6,019,729 A | | 2/2000 | Itoigawa et al. |
| 6,024,704 A | | 2/2000 | Meador et al. |
| 6,030,413 A | * | 2/2000 | Lazarus ..................... 623/1.11 |
| 6,033,366 A | * | 3/2000 | Brockway et al. ............ 600/486 |
| 6,053,873 A | * | 4/2000 | Govari et al. ................ 600/505 |
| 6,076,016 A | | 6/2000 | Feierbach |
| 6,132,456 A | * | 10/2000 | Sommer et al. ............. 607/127 |
| 6,159,156 A | * | 12/2000 | Van Bockel .................. 600/485 |
| 6,231,516 B1 | * | 5/2001 | Keilman et al. ............. 600/485 |
| 6,234,973 B1 | * | 5/2001 | Meador et al. .............. 600/486 |

FOREIGN PATENT DOCUMENTS

| | | |
|---|---|---|
| EP | 0337035 A1 | 10/1989 |
| WO | WO 95/33517 A1 | 6/1995 |
| WO | WO 97/09926 A1 | 3/1997 |
| WO | WO 97/33513 A1 | 3/1997 |
| WO | WO 97/32518 A1 | 9/1997 |
| WO | WO 97/32519 A1 | 9/1997 |

OTHER PUBLICATIONS

Brockway, B.P., et al., "A New Method for Continuous Chronic Measurement and Recording of Blood Pressure, Heart Rate and Activity in the Rat Via Radio-Telemetry"; Clinical and Experimental Hypertension—Theory and Practice, A13(5), pp. 885-895, (1991).

Sato, K., et al., "Evaluation of a New Method Using Telemetry for Monitoring the Left Ventricular Pressure in Free-Moving Rats", J. Pharm. & Tox. Methods; vol. 31, No. 4, pp. 191-198, (Aug. 1994)

van den Buuse, M., "Circadian Rhythms of Blood Pressure, Heart Rate, and Locomotor Activity in Spontaneously Hypertensive Rats as Measured with Radio-Telemetry", Phys. & Behavior; 55(4), pp. 783-787, (1994).

Zimmerman, T.G., "Personal Area Networks: Near-field intrabody communication", IBM Systems Journal (USA), vol. 35 (3-4), pp. 609-617, (1996).

* cited by examiner

IMPLANTABLE SENSOR WITH WIRELESS COMMUNICATION

CROSS-REFERENCE TO RELATED APPLICATION

This application claims priority to, and is a divisional of, U.S. application Ser. No. 09/159,653, filed Sep. 24, 1998, now U.S. Pat. No. 6,409,674.

FIELD OF THE INVENTION

This invention relates generally to an implantable sensor with wireless communication, and particularly, but not by way of limitation, to physiological monitoring of pressure or other parameters in humans and animals using a monitor that is implantable within a heart chamber or elsewhere and is capable of wireless communication of sensor information therefrom.

BACKGROUND

The monitoring of fluid pressure within a body organ provides an important tool for medical research and clinical diagnosis. For example, hydrocephalus and head injuries can cause body fluids to build up within the brain. The resulting fluid pressure buildup can result in death or serious brain damage. In another example, urinary dysfunction can cause fluid pressure to build up in the bladder. In a further example, intrapleural pressure measurements can be used to monitor the respiration of infants who have been identified as being at risk for sudden infant death syndrome.

Blood pressure measurements are particularly important for medical research and diagnosis for a variety of reasons. Such measurements provide researchers with insight into the physiology and functioning of the heart. Blood pressure measurements also provide researchers with useful information regarding the safety and efficacy of pharmaceuticals and the toxicity of chemicals. By transducing blood pressure into a signal waveform, a variety of useful parameters can be extracted. These parameters provide valuable information for the diagnosis of heart disease. Left ventricular (LV) blood pressures measurements are particularly important because the left ventricle chamber of the heart pumps blood to the systemic circulatory system, that is, throughout the rest of the body.

Common parameters extracted from left ventricular blood pressure waveforms include peak systolic pressure (the high pressure peak resulting from a contraction of the left ventricle chamber of the heart), end diastolic pressure (the low pressure valley resulting from expansion of the left ventricle), and maximum dP/dt (a peak value of how fast the pressure (P) changes with time (t) during a contraction of the left ventricle). These blood pressure measurements provide helpful diagnostic information to the physician.

For example, maximum dP/dt provides a measure of the work that is being done by the heart. For certain conditions, such as congestive heart failure (CHF), it is desired to reduce the work load on the heart. The treating physician can determine how effective a therapy is by determining if the treatment regimen has indeed reduced the work load on the heart, as indicated by the maximum dP/dt signal extracted from the left ventricular blood pressure waveform. Measurement of left ventricular blood pressure is also useful for titrating new drugs for treating heart disease, that is, determining the desired dosage or concentration of a new drug. Titrating new drugs requires information on how these drugs are affecting the heart.

For example, beta adrenergic blocking drugs are often effective at treating arrhythmias and improving patient hemodynamics. However, such drugs are difficult to titrate. Because left ventricular blood pressure parameters, such as maximum dP/dt, provide information on how the heart is functioning, monitoring these parameters allows a physician to more easily determine the most appropriate dose of the drug for treating the patient. The maximum dP/dt signal, if available, could also be used as a feedback mechanism in a system that automatically delivers therapy to adjust the work load of the heart. The delivery of therapy is automatically adjusted based on the work load of the heart, as indicated by the maximum dP/dt signal.

In another example, left ventricular blood pressure provides useful information for controlling a cardiac rhythm management system. Cardiac rhythm management systems include, among other things, pacemakers, of pacers. Pacers deliver timed sequences of low energy electrical stimuli, called pace pulses, to the heart. Heart contractions are initiated in response to such pace pulses. By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One example of using a cardiac rhythm management device to control heart rate in proportion to left ventricular blood pressure is described in Mehra U.S. Pat. No. 5,129,394. The '394 patent, however, does not disclose sensing actual left ventricular blood pressure. Instead, it discloses a pressure sensor located in the coronary vein. The coronary vein extends from the right atrium through the heart tissue near the left ventricle. Because of its small size, the coronary vein is difficult to access for inserting a pressure sensor. Moreover, blood pressure sensing in the coronary vein provides only an indirect approximation of the actual left ventricular blood pressure.

Other existing techniques for monitoring left ventricular blood pressure also have drawbacks. One technique of measuring left ventricular blood pressure is described in Brockway et al. U.S. Pat. No. 4,846,191, which is assigned to the assignee of the present application. The '191 patent describes a pressure sensor that is implanted in the abdomen of a laboratory animal. The pressure sensor is connected to an organ, such as the heart or the brain, via a fluid-filled pressure transmitting catheter (PTC). One limitation of this device is that it requires invasive access to the organ in which fluid pressure is to be monitored.

For example, in monitoring left ventricular pressure, one surgical technique for using the device described in the '191 patent involves performing a highly invasive laparotomy procedure. In this procedure, the pressure transmitting catheter is passed through an incision in the diaphragm and an incision into the apex (bottom tip) of the heart. The high blood pressure in the left ventricle further increases the risk of making such incisions directly into the left ventricle. This procedure typically requires a two week recovery period for the laboratory animal. Moreover, because catheterization of the apex involves significant risks, this technique would likely be considered too invasive for human use.

Alternatively, an incision may be made into the aorta, which is the primary artery carrying blood from the left ventricle to the rest of the body. The pressure transmitting catheter is then passed into the aortic incision for measuring blood pressure in the aorta. Aortic incisions are also problematic because of the high blood pressure in the arterial circulatory system. Moreover, measuring blood pressure in the aorta does not provide a direct measurement of blood pressure in the left ventricle; such information is unavailable, for example, when the aortic valve is closed. Alternatively, the pressure transmitting catheter could be passed through the aortic valve into the left ventricle. However, leaving the pressure transmitting catheter extending through the aortic valve for a long period of time risks damage to the aortic valve as a result of the high blood pressure in the left ventricle. Thus, this procedure is also likely unsuitable for human use, particularly for chronic left ventricular blood pressure monitoring, i.e., monitoring over an extended period of time.

Another technique for measuring left ventricular blood pressure is described in Pohndorf et al. U.S. Pat. No. 5,353,800. A distal end of a pressure sensing lead is transvenously introduced into the right ventricle of the patient's heart. A hollow needle at the distal end of the lead is punched through the ventricular septum, that is, through the wall separating the right and left ventricles. This provides access to the left ventricle for sensing pressure gradients that are communicated through the hollow needle to a pressure sensor that is outside of the left ventricle. Because this procedure involves invasively forming an opening in the septum, it creates significant risks for human cardiac patients who are likely already very sick and vulnerable to such risks.

A further technique for measuring left ventricular blood pressure uses a pressure sensing catheter, such as a "Millar catheter," available from Millar Instruments, Inc., of Houston, Tex. The pressure sensing catheter is passed through the left atrium and through the mitral valve (which separates the left atrium and left ventricle) into the left ventricle. As discussed above, however, high blood pressures exist in the left ventricle, which would likely result in damage to the mitral valve if the catheter were left interposed in the mitral valve for a long period of time. As a result, if a sequence of successive measurements is to be obtained over a long period of time, the patient must undergo recatheterization for each measurement. However, catheterization itself involves risk, discomfort, and expense, making multiple catheterizations of the patient very undesirable.

In summary, present techniques for measuring left ventricular pressure are too invasive for human use and unsuitable for use over an extended period of time. Physicians and researchers need less invasive techniques for chronic measurement of left ventricular blood pressure, both for diagnosing heart conditions and for determining whether therapy delivered to the heart is adequate for effectively treating the patient's symptoms.

SUMMARY

The present system provides, among other things, a less invasive implantable sensor device capable of wirelessly communicating sensor information. The sensor is implantable in a heart chamber, in other body organs and body cavities, and elsewhere within a living organism. One example includes a blood pressure monitoring device that is suitable for use over an extended period of time in the left ventricle for wirelessly communicating blood pressure information therefrom. This provides less invasive chronic pressure measurements in the left ventricle. As a result, the risk of obtaining such important measurements is reduced. This enables a physician to more accurately diagnose and treat serious heart conditions. It also enables a biomedical researcher to monitor sensor signals in animal research studies.

In one example, the wirelessly communicated left ventricular blood pressure information is used to control the delivery of therapy by a cardiac rhythm management device. In another example, the present system advantageously allows a physician to obtain a sequence of left ventricular blood pressure measurements over a long period of time. By contrast, using a pressure sensing catheter for obtaining such measurements over a long period of time risks damaging heart valves because of the high blood pressures that exist in the left ventricle. Because the present system allows long term monitoring, it can be used, for example, in assessing circadian variations in physiological data over a period of time. Such information is potentially valuable in diagnosing and treating patients. See, e.g., Brian P. Brockway, Perry A. Mills, and Sylvia H. Azar, "A New Method For Continuous Chronic Measurement and Recording of Blood Pressure, Heart Rate, and Activity in the Rat via Radio-Telemetry," Clinical and Experimental Hypertension—Theory and Practice, A13(5), pp. 885-895 (1991), which is incorporated herein by reference in its entirety.

Certain particular embodiments of the invention are summarized below, by way of illustrative example, but not by way of limitation. The scope of the invention should, therefore, be determined with reference to the appended claims, along with the full scope of equivalents to which such claims are entitled.

One aspect of the invention provides an apparatus for sensing a parameter in a heart chamber in a heart in a living organism. The apparatus includes a sensor and a wireless communication circuit. The sensor is adapted for being disposed in the heart chamber. The sensor provides a sensor signal based on the parameter sensed in the heart chamber. The wireless communication circuit is adapted for being disposed in the heart chamber. The communication circuit is coupled to the sensor and transmits information out of the heart chamber based on the sensor signal. The wireless communication techniques include radio-telemetry, reactive coupling, passive transponders, and intracorporeal conductive communication.

In one embodiment, the sensing apparatus includes a housing carrying the sensor and the communication circuit and at least one stabilizer that is coupled to the housing. Also included in the housing is a battery which, in one embodiment, is recharged by energy received from outside the heart chamber. A receiver, external to the heart chamber, is communicatively coupled to the communication circuit for receiving the information based on the sensor signal. In one embodiment, the receiver is carried by a cardiac rhythm management system, and therapy delivered by the cardiac rhythm management system is adjusted according to information wirelessly received from the sensor device implanted in the heart chamber. In another embodiment, the receiver is coupled to a computer that analyzes or displays the information from the sensor. In one embodiment, the sensor is a pressure transducer, however, other sensors may also be used.

Another aspect of the invention includes a method of sensing a parameter (e.g., blood pressure) in a heart chamber in a heart in a living organism. A physical manifestation of the parameter in the heart chamber is received at a sensor disposed within the heart chamber, where it is transduced into a sensor signal. Information based on the sensor signal is wirelessly communicated from the heart chamber. A further embodiment includes translumenally disposing the sensor in the heart chamber.

One embodiment of communicating the information includes using a passive transponder. In this technique, energy is received from outside the heart at a passive transponder that is in the heart. The passive transponder is powered from the energy received from outside the heart chamber. Information is transmitted from the heart chamber using the powered passive transponder. In another embodiment, energy received from outside the heart chamber is used to recharge a battery that is located in the heart chamber.

Another embodiment of communicating information includes using intracorporeal conductive communication, which uses the living organism as the conductor. In this technique, a current is conducted through at least a portion of the living organism. A signal that is based on this current is received at a receiver that is outside the heart chamber. In one embodiment, the receiver is carried by an implantable medical device located within the living organism such as, for example, a cardiac rhythm management device. Therapy delivered by the cardiac rhythm management device is adjusted based on the signal received by intracorporeal conductive communication or other wireless communication technique. In another embodiment, the receiver is external to the living organism, and information is stored in a memory in the receiver.

Another aspect of the invention provides a method. The method includes inducing a current between first electrodes implanted in a living organism. The current at the first electrodes is modulated with a data signal. A signal based on the current is demodulated at second electrodes. In one embodiment, the second electrodes are also implanted in the living organism.

Another aspect of the invention provides a catheter. The catheter includes an elongate member having first and second ends. The first end of the elongate member includes a cavity adapted for carrying an implantable measurement device that includes a wireless communication circuit. The elongate member also includes a lumen extending substantially between the cavity and the second end of the elongate member. An engaging member is carried by the cavity. The engaging member is extendable outwardly from the cavity at the first end of the elongate member. The engaging member is operatively coupled to a manipulator at the second end of the elongate member. The engaging member is adapted for engaging the implantable measurement device. In one embodiment, portions of the elongate member are flexible such that the catheter is adapted for translumenal access to a heart chamber. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views.

This document describes, among other things, an implantable sensor, such as a pressure monitor. The sensor device is implanted in a heart chamber (or elsewhere) and wirelessly communicates information therefrom. In one embodiment, the sensor device is capable of providing less invasive chronic measurements of pressure, such as, by way of example, but not by way of limitation, measurements of blood pressure in the left ventricle of the heart. The implantable pressure monitor reduces the risk of obtaining such important measurements, enabling a physician to more accurately diagnose and treat serious heart conditions.

System Overview

Figure 1:
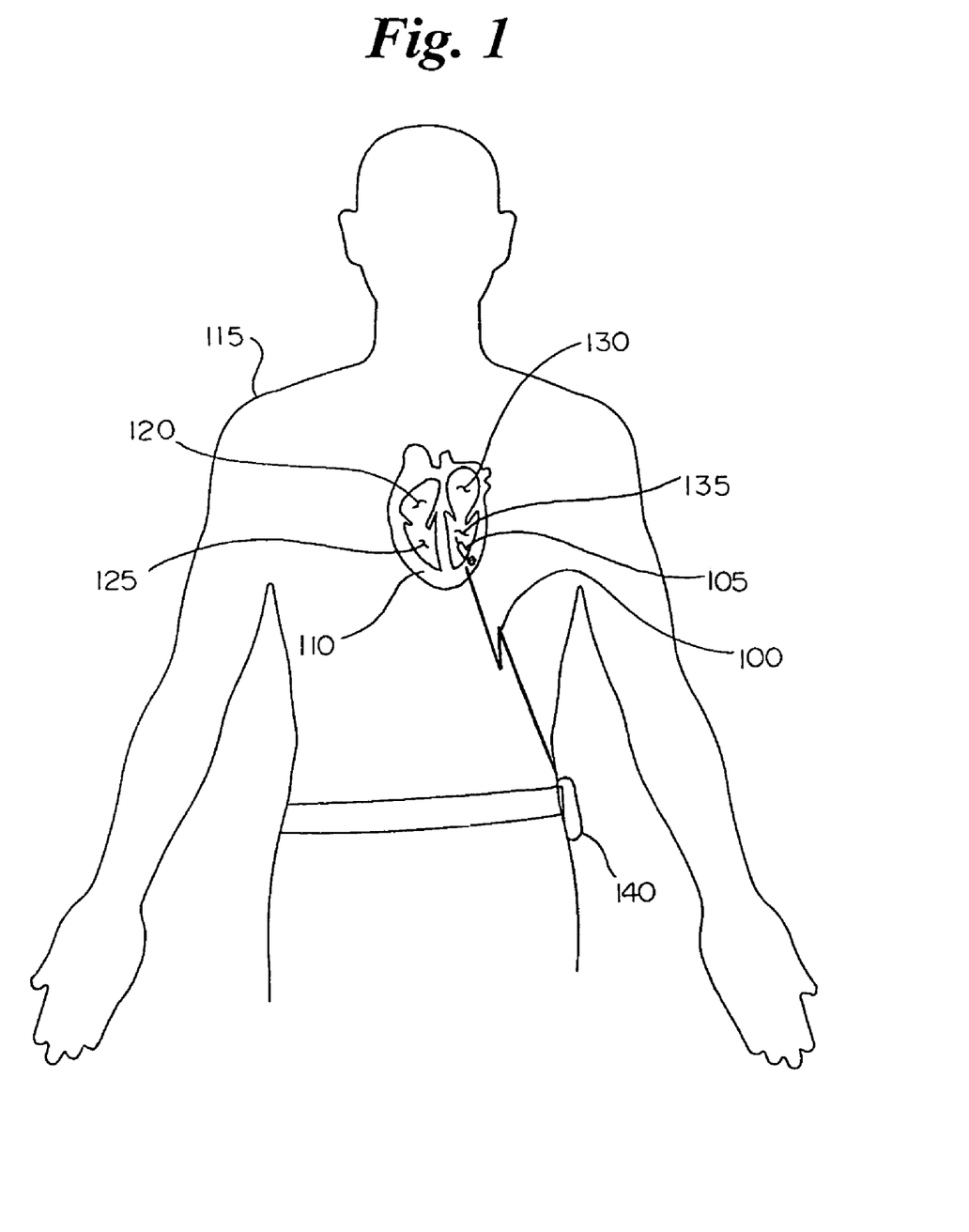
FIG. 1 is a schematic diagram illustrating generally one embodiment of portions of a sensor system, such as a pressure monitor system, and an environment in which it is used.

FIG. 1 is a schematic diagram illustrating generally, by way of example, but not by way of limitation, one embodiment of portions of a sensor system, such as pressure monitor system 100, and one environment in which system 100 is used. In FIG. 1, system 100 includes a sensor device, such as an implantable pressure monitor device 105. Device 105 is introduced into a living organism, such as in a heart chamber or other organ or body cavity. Miniature implantable device 105 is capable of measuring internal body pressure, such as in humans or animals. Aspects of one embodiment of device 105 and its operation are described in Brockway et al. U.S. Pat. No. 4,846,191 entitled "Device For Chronic Measurement of Internal Body Pressure," which is assigned to the assignee of the present application, and which is incorporated herein by reference in its entirety.

In FIG. 1, device 105 is implanted in a heart 110 of a human patient 115. Heart 110 includes several heart chambers, such as a right atrium 120, a right ventricle 125, a left atrium 130, and a left ventricle 135. In this particular example, device 105 is implanted, using a placement catheter, inside left ventricle 135 where it is stabilized, such as by securing the device 105 to an interior wall of left ventricle 135. However, in other embodiments, device 105 is implanted in one of the right atrium 120, right ventricle 125, left atrium 130, or within other organs or body cavities. Device 105 can be introduced into the body translumenally (e.g., transvenously or transarterially), endoscopically, laparoscopically, or otherwise (e.g., during open heart surgery).

In this embodiment, system 100 also includes an implantable or external receiver 140 or other receiver, transceiver, transponder, or communication device. Device 105 wirelessly communicates pressure information from the organ in which device 105 is located, such as by using radio telemetry or any other wireless communication technique. In FIG. 1, left ventricular blood pressure information is communicated by device 105 and received by an external receiver 140 worn by the patient. In one embodiment, receiver 140 includes a memory or recording device for storing the pressure information received from device 105. In a further embodiment, receiver 140 includes a real time clock for time-stamping the pressure information with the time at which the information is received at receiver 140.

Figure 2:
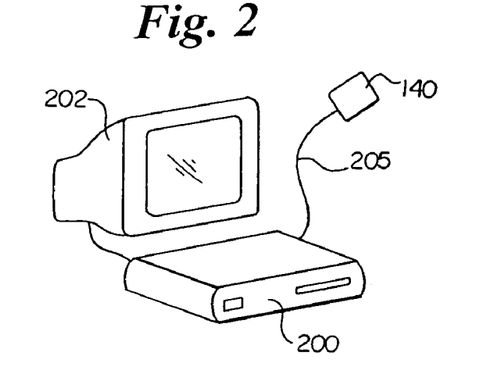
FIG. 2 is a schematic diagram illustrating generally an embodiment of certain external portions of the system.

FIG. 2 is a schematic diagram illustrating generally, by way of example, but not by way of limitation, another embodiment of portions of system 100. In FIG. 2, pressure information that was stored in the memory or recording device of receiver 140 is transferred into computer 200, such as via an electrical coupling cable 205, or alternatively via optical communication, or using any other wired or wireless communication technique. In one embodiment, computer 200 includes a processor for performing statistical or other signal processing or analysis of the pressure information. In another embodiment, computer 200 includes a display 202 for allowing the physician or other care giver to review and analyze the pressure data. In one example, display 202 includes diagnostic indicators based on analysis of the pressure data by computer 200.

In a further embodiment, computer 200 includes a memory for archival of raw or processed pressure information. For example, the pressure information can be electronically appended to the patient's medical record in a computer database.

Implantable Pressure Monitor

Figure 3A:
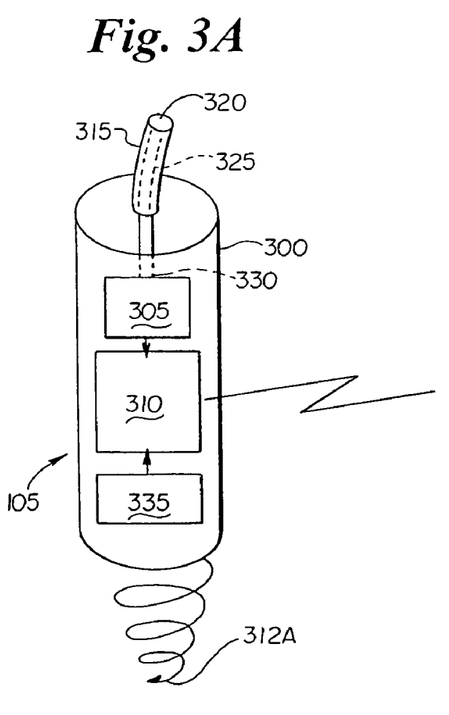
FIG. 3A is a schematic/block diagram illustrating generally one embodiment of a portion of an implantable sensor device, such as an implantable pressure monitor device including a corkscrew stabilizer.

FIG. 3A is a schematic/block diagram illustrating generally, by way of example, but not by way of limitation, one embodiment of device 105. In this embodiment, device 105 includes a housing 300 carrying a sensor, such as pressure transducer 305, and a communication circuit 310. Housing 300 is adapted for implantation in a living organism such as a human or animal. In one example, housing 300 is implanted within a body cavity or an organ, such as within a heart chamber (e.g., left ventricle 135) of heart 110.

In one embodiment, device 105 includes a stabilizer 312A extending outward from housing 300 to stabilize or secure device 105 at a particular location in the heart chamber or other organ in which device 105 is implanted. FIG. 3A illustrates a corkscrew stabilizer 312A which, in one embodiment, includes a solid coiled needle extending longitudinally outward from housing 300. By rotating device 105, corkscrew stabilizer 312A is screwed into the wall of the heart chamber or other organ in which device 105 is disposed, thereby securing device 105 at a particular location in the body. The corkscrew stabilizer 312A is used with or without one or more barbs. The barbs are located, for example, at a tip distal from device 105, or at different locations along the helical length of stabilizer 312A. In one embodiment, the surface of corkscrew stabilizer 312A is coated or otherwise prepared to promote the growth of fibrotic tissue to reliably secure device 105 to the heart wall or other desired location.

Figure 3B:
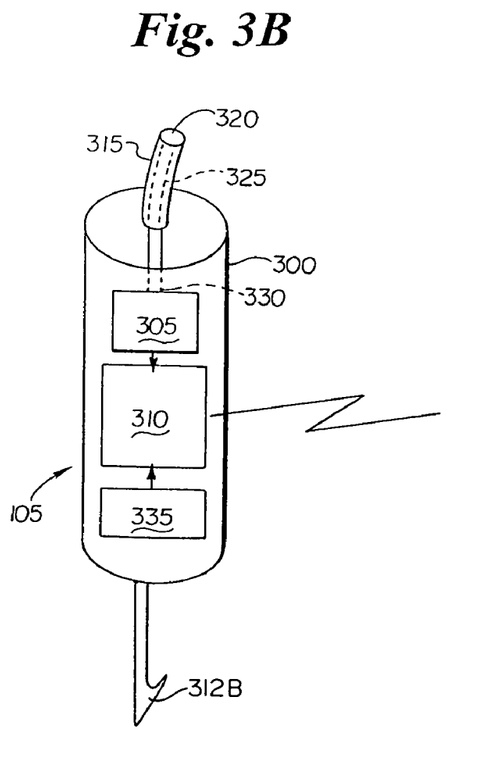
FIG. 3B is a schematic/block diagram illustrating generally one embodiment of an implantable sensor device, such as an implantable pressure monitor device including a harpoon or barbed stabilizer.
Figure 3C:
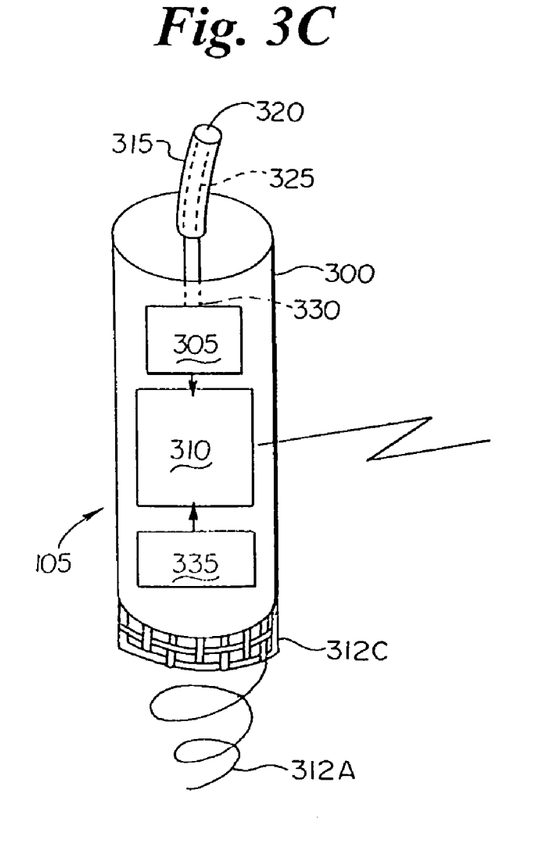
FIG. 3C is a schematic/block diagram illustrating generally one embodiment of an implantable sensor device, such as an implantable pressure monitor device including a mesh stabilizer and a corkscrew stabilizer.
Figure 3D:
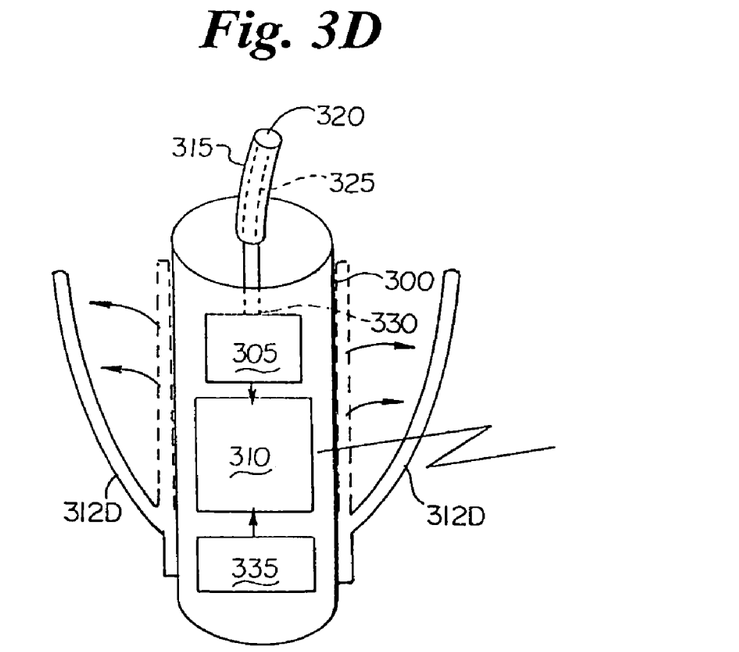
FIG. 3D is a schematic/block diagram illustrating generally one embodiment of an implantable sensor device, such as an implantable pressure monitor device including a deformable stabilizer.

FIG. 3B illustrates generally one embodiment of a harpoon stabilizer 312B, providing an approximately straight outward extension from housing 300, and including a barb or hook at its distal tip. FIG. 3C illustrates generally one embodiment of a mesh stabilizer 312C, extending outward from or integrally formed with housing 300. Mesh stabilizer 312C also promotes the ingrowth of adjacent fibrous tissue to assist in securing device 105 at a particular location. FIG. 3D illustrates generally one embodiment of a flexible or expanding deformable stabilizer 312D. In one embodiment, stabilizer 312D is made of a flexible, spring-like, or deformable material or a "memory metal." As illustrated in FIG. 3D, stabilizer 312D maintains a compact shape during implantation, but deforms or expands in profile after device 105 is implanted into the heart chamber or other body cavity. As a result of this deformation or expansion, stabilizer 312D tends to hold device 105 within the body cavity in which it is implanted. The above-discussed stabilizers 312 can also be used in combination with each other, such as illustrated in FIG. 3C.

FIGS. 3A-3D illustrate particular embodiments of device 105 in which the internal pressure of the organ is provided to pressure transducer 305 via a pressure communication apparatus such as, by way of example, but not by way of limitation, a flexible or rigid pressure transmitting catheter (PTC) 315. In one embodiment, pressure transmitting catheter 315 senses a pressure at one or more pressure-sensitive mechanisms (e.g., a diaphragm, gel-like cap, or other compliant structure) at its distal tip 320. Pressure transmitting catheter 315 communicates the pressure, via a bore, shaft, or lumen 325, to its proximal end 330 that interfaces with transducer 305. Lumen 325 extends substantially between distal tip 320 and proximal end 330 of pressure transmitting catheter 315. In one embodiment, lumen 325 is filled with a pressure-transmitting medium, such as a fluid of any viscosity, a gel-like material, a combination of fluid and gel-like material, or any other flowable medium. In one embodiment, by way of example, but not by way of limitation, distal tip 320 includes a biocompatible and pressure-transmitting gel cap for transmitting substantially steady-state and/or very low frequency pressure variations, and distal tip 320 also includes a thin-wall compliant structure for transmitting pressure variations at higher frequencies. Lumen 325 is filled with a pressure-transmitting fluid retained within lumen 325 by the gel cap. The gel cap also prevents body fluids from entering lumen 325. Similarly, in one embodiment, proximal end 330 includes one or more pressure-transmitting mechanisms (e.g., a diaphragm, gel-like cap, or other compliant structure), which also retains the pressure-transmitting fluid in lumen 325. Although one embodiment of device 105 includes pressure transmitting catheter 315, the technique of communicating pressure to pressure transducer 305 is not limited to using pressure transmitting catheter 315. For example, device 105 alternatively provides a pressure transmitting mechanism that is integrally formed with housing 300 of device 105 rather than extending outwardly therefrom. Other embodiments of device 105 include the use of any other technique of receiving pressure at pressure transducer 305.

Pressure transducer 305 receives the pressure communicated by pressure transmitting catheter 315, or by any other pressure communication mechanism, at the interface at its proximal end 330. In response, pressure transducer 305 provides an electrical pressure signal that includes pressure information, such as steady-state pressure or variations in pressure. In one embodiment, pressure transducer 305 includes a semiconductor resistive strain gauge, the resistance of which varies according to the pressure communicated by pressure transmitting catheter 315. Transducer 305 is electrically coupled to communication circuit 310 and provides the electrical pressure signal to communication circuit 310.

Communication Techniques

Communication circuit 310 wirelessly transmits pressure information from device 105 to remote receiver 140 (or other receiver, transceiver, transponder, or communication device) by radio telemetry or any other wireless data communication technique. In one embodiment, communication circuit 310 includes or is coupled to an antenna for wireless communication. However, the antenna need not be located within communication circuit 310. In another embodiment, communication circuit 310 also includes signal processing circuits, such as amplification and filtering circuits that process the electrical pressure signal received from pressure transducer 305, or analog-to-digital conversion circuits, or a microprocessor or other circuit for performing data analysis or data compression. In a further embodiment, communication circuit 310 also includes a memory device for storing the pressure information, other data, or operating parameters of device 105. In yet another embodiment, communication circuit 310 includes a real-time clock for time-stamping the pressure information.

In one embodiment, at least one of communication circuit 310 or transducer 305 is powered by an internal power source such as a lithium or other suitable battery 335. In another embodiment, communication circuit 310 is a passive transponder that is not powered by an internal power source. Instead, communication circuit 310 receives energy wirelessly from a remote source, such as an energy source external to the body of the patient in which device 105 is implanted. Communication circuit 310 is powered by the energy that it receives wirelessly from the external source. In another embodiment, battery 335 is rechargeable and device 105 includes an energy reception circuit that is coupled to battery 335. The energy reception circuit in device 105 wirelessly receives energy from a remote source, such as an energy source that is external to the body of the patient in which device 105 is implanted. The energy that is received by the energy reception circuit in device 105 is used by the energy reception circuit to recharge battery 335.

In one example of passive transponder technology, communication circuit 310 includes a first inductance, such as a coil. A second inductance, such as a coil, is placed outside the body, for example, at a location that is close to the site of the implanted device. The first and second inductances are inductively coupled for wireless energy transmission from the external second inductance to the implanted first inductance, and for wireless data communication from the implanted first inductance to the external second inductance. System 100 may incorporate other passive transponder techniques as well.

In one embodiment, communication circuit 310 wirelessly communicates pressure information from device 105 to external remote receiver 140 using an intracorporeal conductive communication device (also referred to as "near-field intra-body communication" or a "personal area network"). In this document, wireless communication refers to any communication technique that does not use a wire or optical fiber. Wireless communication includes either or both of unidirectional and/or bidirectional communication. The unidirectional or bidirectional communication is carried out between any combination of implanted and/or external communication devices. In various embodiments, certain ones of the communication devices are carried by implanted sensor devices (such as an implanted pressure monitor), implanted medical devices (such as an implanted cardiac rhythm management device), and external communication devices for communication therebetween. Wireless communication includes, but is not limited to: radio telemetry, reactive coupling, and intracorporeal conductive communication. In this document, intracorporeal conductive communication refers to any communication technique that uses a living organism (e.g., the body of a human or animal) as a conductor for communicating data. In one embodiment, wireless communication is used to program operating parameters in implanted device 105.

In one example of an intracorporeal conductive communication device, communication circuit 310 is electrically coupled to electrodes located on housing 300 and insulated from each other. Communication circuit 310 capacitively couples a very low (e.g., less than a stimulation threshold of heart 110) displacement current that is conducted through the body to remote receiver 140. The current is modulated with a data signal. The data signal includes the pressure information or other data to be wirelessly communicated from the implanted medical device 105. In this embodiment, the resulting current is detected at remote receiver 140 by electrodes that contact the body of patient 115 during the wireless communication from device 105. The detected current is demodulated to obtain the pressure information or other data. The use of intracorporeal conductive communication techniques is described in Coppersmith et al. U.S. Pat. No. 5,796,827 entitled "System and Method for Near-Field Human-Body Coupling For Encrypted Communication With Identification Cards," and in T. G. Zimmerman, "Personal Area Networks: Near-field intrabody communication," IBM Systems Journal, Vol. 35, No. 3 & 4, 1996, each of which is incorporated herein by reference in its entirety.

In one embodiment, system 100 includes, among other things, communicating information from any implanted medical device to an external remote receiver 140 using intracorporeal conductive communication (i.e., using the body as a conductor). Examples of such implanted medical devices include, but are not limited to: pressure monitors, cardiac pacemakers, defibrillators, drug-delivery devices, and cardiac rhythm management devices.

Figure 4:
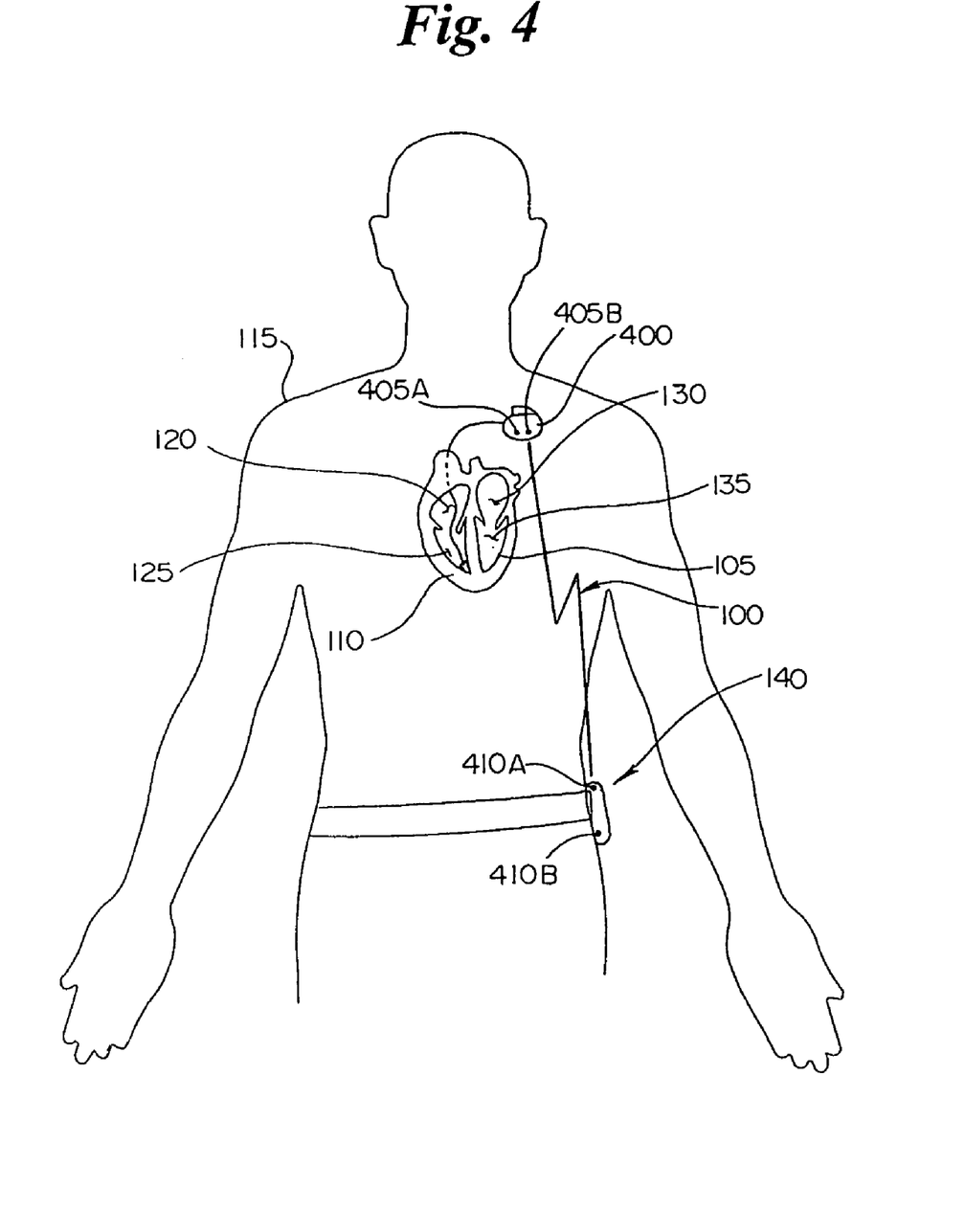
FIG. 4 is a schematic diagram illustrating generally one embodiment of the present system using wireless communication, such as intracorporeal conductive communication, between an implanted medical device, such as cardiac rhythm management system, and an external remote receiver.

FIG. 4 is a schematic diagram illustrating generally, by way of example, but not by way of limitation, one embodiment of system 100 using either unidirectional or bidirectional intracorporeal conductive communication between an implanted medical device, such as cardiac rhythm management device 400, and an external remote receiver 140. This includes, for example, intracorporeal conductive communication of data from electrodes 405A-B at the cardiac rhythm management device 400 to electrodes 410A-B at the external remote receiver 140, as well as programming operating parameters of cardiac rhythm management device 400 based on instructions received via intracorporeal conductive communication from external remote receiver 140.

Figure 5:
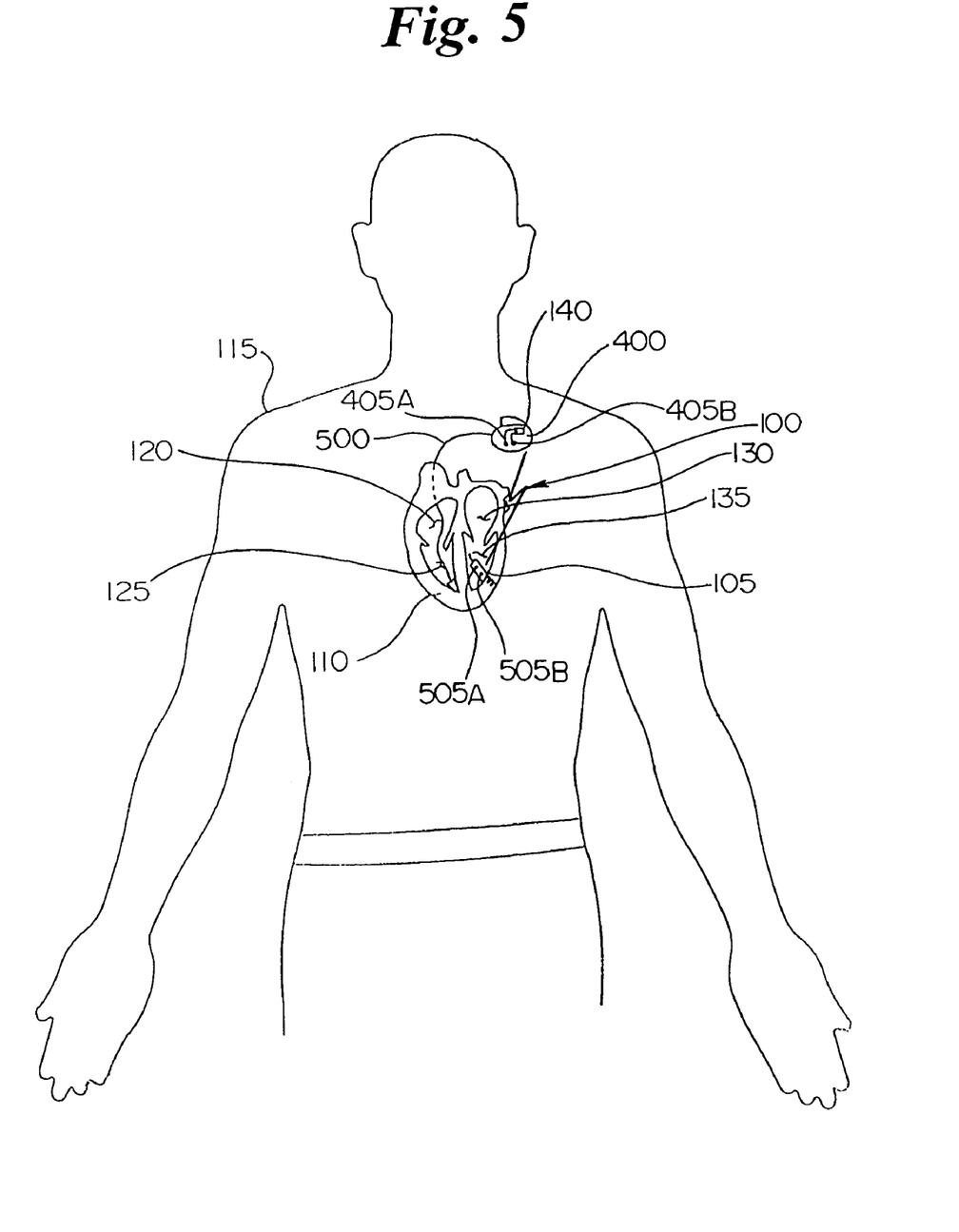
FIG. 5 is a schematic diagram illustrating generally one embodiment of the present system using wireless communication, such as intracorporeal conductive communication, between an implanted sensor device and an implanted remote receiver that is carried by an implanted medical device such as by cardiac rhythm management system

FIG. 5 is a schematic diagram illustrating generally, by way of example, but not by way of limitation, another embodiment of system 100 using either unidirectional or bidirectional intracorporeal conductive communication between electrodes 505A-B at pressure monitor device 105, which is implanted in left ventricle 135, and electrodes 405A-B coupled to an implanted remote receiver 140 carried by an implanted medical device, such as by cardiac rhythm management device 400. In one embodiment, cardiac rhythm management device 400 includes a therapy generator that is coupled to heart 110 through a leadwire. In this embodiment, device 105 senses left ventricular blood pressure and communicates, via intracorporeal conductive communication, left ventricular blood pressure information to cardiac rhythm management device 400 where it is received by implanted receiver 140. Based on the received pressure information, cardiac rhythm management device 400 adjusts therapy delivered to heart 110. In one example, cardiac rhythm management device 400 is a pacer or pacer/defibrillator that adjusts the rate of delivering electrical pacing pulses to heart 110 via leadwire 500 based on the left ventricular pressure information received from device 105. In another example, cardiac rhythm management device 400 is a defibrillator or pacer/defibrillator that delivers antitachyarrhythmia therapy to heart 110 based on the left ventricular pressure information received from device 105. Similarly, system 100 includes using intracorporeal conductive communication to transmit information to device 105 from another implanted medical device, such as cardiac rhythm management device 400. Moreover, the embodiments described with respect to FIGS. 4 and 5 can be combined for communication between any of one or more implanted medical devices, one or more implanted sensor devices such as device 105, and/or one or more external or implanted remote receivers 140.

Implantation and Use

Figure 6:
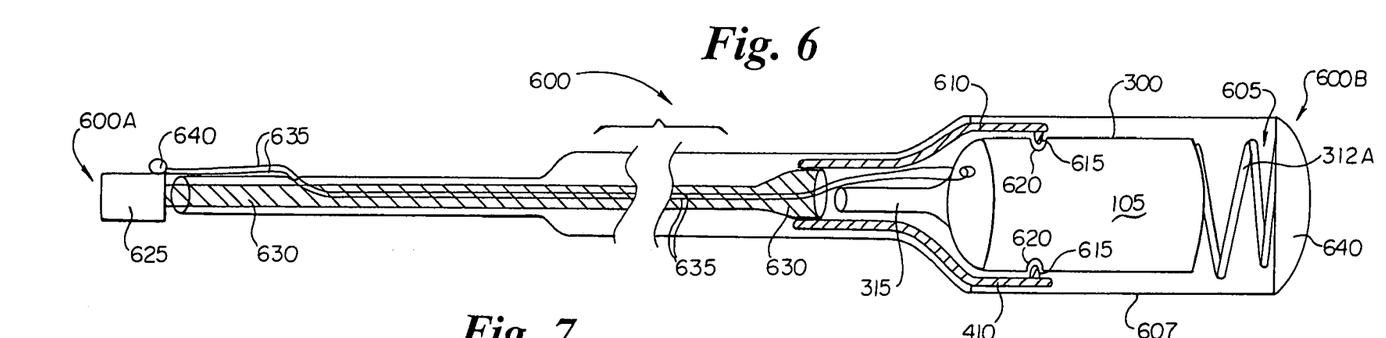
FIG. 6 is a cross-sectional schematic diagram illustrating generally one embodiment of a placement catheter for implanting a sensor device, such as an implantable pressure monitor device.

FIG. 6 is a cross-sectional schematic diagram illustrating generally, by way of example, but not by way of limitation, one embodiment of a placement catheter 600 for implantably disposing device 105 in a heart chamber, such as left ventricle 135. Catheter 600 includes an at least partially flexible elongate member having a proximal end 600A that is manipulated by the user. Catheter 600 also includes a distal end 600B of the elongate member that is inserted in the patient 115. In one embodiment, the distal end 600B of catheter 600 includes a cavity 605 carrying at least a portion of device 105. Cavity 605 is circumferentially encompassed by a sheath 607 that, in one embodiment, is open at distal end 600B of catheter 600.

Catheter 600 also includes at least one engaging member, such as plunger 610. Plunger 610 engages device 105. In one example, an inner surface of plunger 610 includes protrusions, such as pins 615, that engage receptacles 620 or other indentations in housing 300 of device 105. Plunger 610 is controlled at proximal end 600A of catheter 600 by a manipulator, such as handle 625. Handle 625 is coupled to plunger 610 by a coupling member 630, such as one or more rods or cables extending longitudinally within catheter 600. Plunger 610 is capable of longitudinal motion toward and away from distal end 600B of catheter 600, so that device 105 can be advanced from or retracted toward cavity 605. Plunger 610 is also capable of rotational motion, by manipulating handle 625, so that corkscrew stabilizer 312A can be rotatably screwed into tissue such as the heart wall. Pins 615 engage receptacles 620 to ensure that device 105 rotates together with plunger 610.

In one embodiment, catheter 600 also includes a safety tether 635, which is looped through an opening or other feature in housing 300 of device 105. Tether 635 extends longitudinally through catheter 600 toward proximal end 600A, where the looped tether 635 is knotted or otherwise secured at a tether keep 640 on handle 625 or elsewhere. Tether 635 secures device 105 to catheter 600 until final release of device 105 is desired, at which time tether 635 is cut.

In another embodiment, catheter 600 includes a convex cap 640 at distal end 600B. Convex cap 640 eases the translumenal travel of catheter 600 through a blood vessel or other constriction. In one example, cap 640 is hinged to catheter 600, such as at sheath 607, so that cap 640 opens outwardly from distal end 600B when device 105 is pushed out of cavity 605. In another example, cap 640 includes one or more deformable flaps that similarly open outwardly to allow device 105 to be advanced out from cavity 605 by pushing device 105 against cap 640. In a further embodiment, cap 640 includes a material that is soluble in body fluids after a predetermined time period. In this embodiment, cap 640 dissolves after catheter 600 is translumenally guided to left ventricle 135 or other desired location. After cap 640 dissolves, device 105 is advanced longitudinally outward from cavity 605 at distal end 600B of catheter 600. In another embodiment of the invention, cap 640 is omitted such that cavity 605 is open to distal end 600B of catheter 600 even during translumenal insertion.

In one example, catheter 600 is used to place device 105 in a heart chamber, such as left ventricle 135. One such technique includes inserting catheter 600 into the patient 115, such as via the subdlavian artery. Catheter 600 is translumenally guided through the artery, through the left atrium, and through the mitral valve until its distal end 600B is within left ventricle 135. Progress of the catheter 600, as it travels from the insertion point to the left ventricle 135, is typically monitored on a display using fluoroscopy. This assists the physician in translumenally steering catheter 600 along the proper path to a desired location in left ventricle 135. In the embodiment of device 105 illustrated in FIG. 3A, which includes a corkscrew stabilizer 312A, sheath 607 and/or cap 640 prevents the sharp tip of corkscrew stabilizer 312A from damaging the blood vessel while device 105 is being translumenally maneuvered through the blood vessel.

In one embodiment, placement catheter 600 has high torsional stability and is steerable. In this embodiment, sheath 607 and portions of catheter 600 near its distal end 600B are substantially rigid. Catheter 600 is adapted for receiving, at its proximal end 600A, a removable stylet that extends longitudinally along catheter 600. The stylet extends approximately to (or slightly beyond) a distal end of coupling member 630. A straight stylet is typically employed until distal end 600B of catheter 600 enters heart 110. Then, the straight stylet is removed from catheter 600 and a stylet having a curved or bent distal end is inserted in its place. By rotating the bent stylet as catheter 600 is advanced into heart 110, the distal end 600B of catheter 600 is directed to the desired location in left ventricle 135 or other heart chamber.

When device 105 is positioned at a desired location in left ventricle 135, plunger 610 is advanced slightly so that corkscrew stabilizer 312A protrudes outwardly from cavity 605 and contacts the heart wall in the interior of left ventricle 135. Handle 625 is rotated which, in turn, rotates plunger 610 together with device 105, such that corkscrew stabilizer 312A is screwed into the heart wall to secure device 105 in position (e.g., at the apex of left ventricle 135 or other desired location). After securing device 105, plunger 610 is advanced further. Plunger 610 is designed to open outwardly when it is extended outside of sheath 607. As a result, pins 615 disengage from receptacles 620, releasing the grip of plunger 610 on device 105. Tether 635 is then cut (at proximal end 600A of catheter 600) and removed, thereby releasing device 105. Catheter 600 is then withdrawn from the subdlavian artery.

Figure 7:
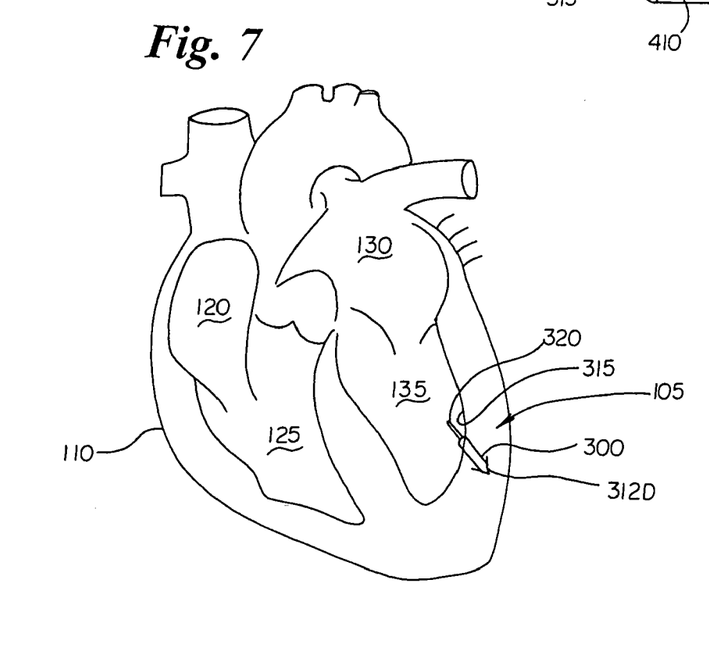
FIG. 7 is a schematic diagram illustrating another embodiment of an implantable sensor device, such as a pressure monitor, having a housing that is substantially implanted within tissue, such as the interior wall of a heart chamber.

FIG. 7 is a schematic diagram illustrating generally, by way of example, but not by way of limitation, another embodiment of device 105 and an environment in which it is used. In FIG. 7, housing 300 of device 105 is substantially implanted within the myocardium at the interior wall of left ventricle 135 of heart 110. The pressure transmitting catheter 315 portion of device 105 extends outwardly from housing 300 into left ventricle 135 for sensing blood pressure its distal tip 320. In this embodiment, deformable stabilizer 312D is integrated with a sharpened end of housing 300 so that housing 300 can be advanced into the heart wall. Then, the deformable stabilizer 312D is expanded in a spring-like fashion to secure device 105 at the desired location. Device 105 is implanted using a placement catheter 600 as described with respect to FIG. 6. In one embodiment, housing 300 is designed to promote fibrous ingrowth, such as by properly preparing housing 300 with a coating and/or surface roughening, or by incorporating a mesh or fabric into the outer surface of housing 300.

Figure 8:
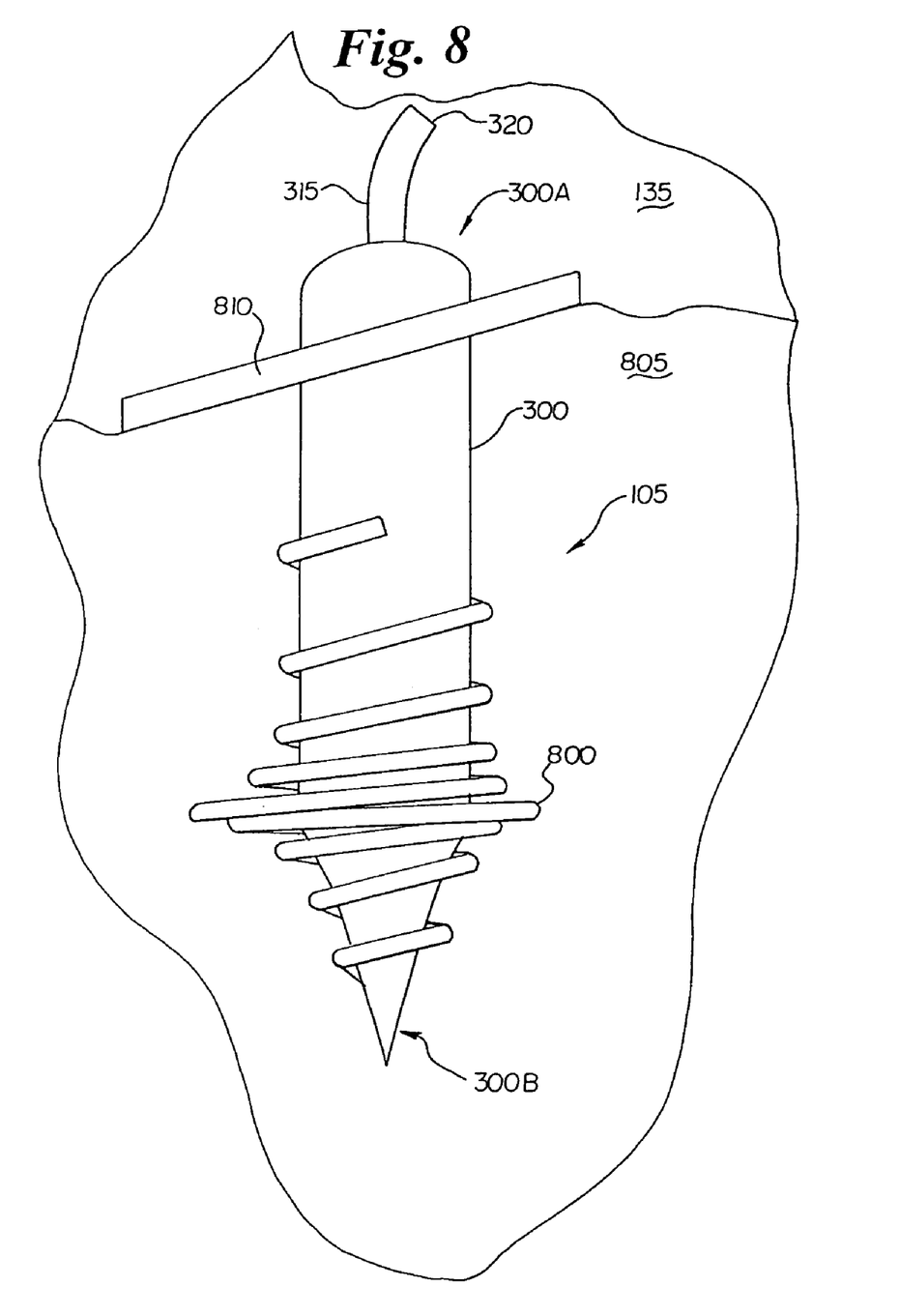
FIG. 8 is a schematic diagram illustrating generally another embodiment of a sensor device for implantation substantially within tissue and having a substantially flexible anchor.

FIG. 8 is a schematic diagram illustrating generally, by way of example, but not by way of limitation, another embodiment of device 105 that is capable of being implanted substantially within the interior wall of left ventricle 135 of heart 110. In this embodiment, device 105 includes a helical anchor 800 surrounding a portion of device 105. In one embodiment, anchor 800 includes a highly elastic metal such as, for example, a memory metal such as nitinol. A spring constant of anchor 800 is low enough to allow anchor 800 to conform to housing 300 of device 105 while torsional force is being applied to insert device 105 into the myocardial tissue 805 or other tissue. Upon release of this torsional force, anchor 800 deforms, such as, for example, by returning to its original shape. This results in the application of force to the surrounding myocardial tissue 805 for securing a portion of device 105 to the tissue. In one embodiment, more than one anchor 800 is included such as, for example, an anchor 800 at both proximal end 300A and distal end 300B of housing 300 of device 105. In another embodiment, housing 300 of device 105 includes a head 810 portion at proximal end 300A. Head 810 limits the advance of device 105 within myocardial tissue 805. This ensures that device 105 has access to the left ventricle 135 or other heart chamber to allow accurate blood pressure measurements in the heart chamber. This also reduces the risk of fibrous tissue growing over the pressure-sensitive portion of device 105, such as pressure transmitting catheter 315.

Figure 9:
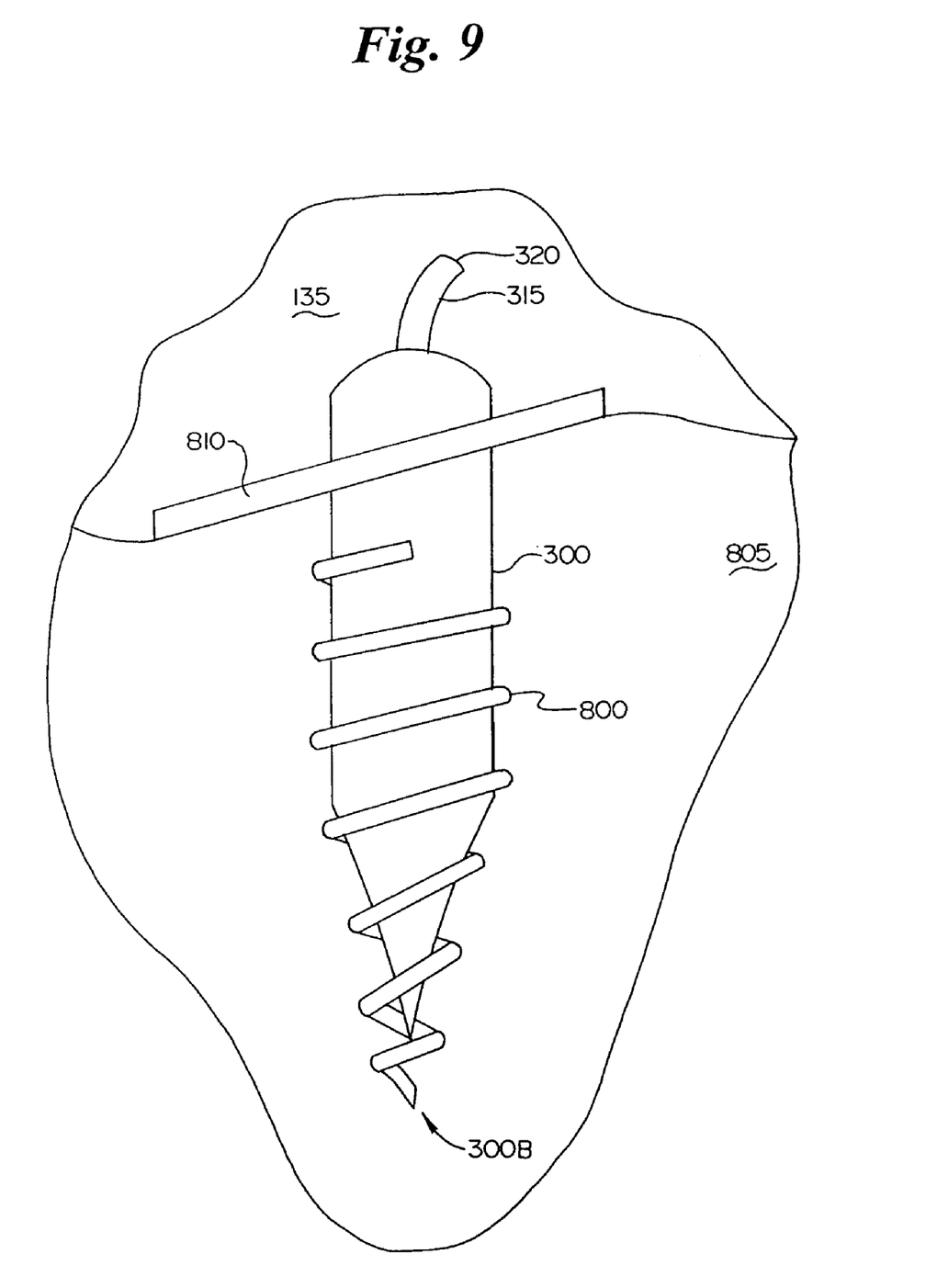
FIG. 9 is a schematic diagram illustrating generally another embodiment of a sensor device for implantation substantially within tissue and having a substantially rigid anchor.

FIG. 9 is a schematic diagram illustrating generally, by way of example, but not by way of limitation, another embodiment of device 105 that is capable of being implanted substantially within myocardial tissue 805. In this embodiment, device 105 includes a substantially rigid helical metal coil (e.g., a titanium coil) anchor 800 surrounding a portion of housing 300 of device 105. Anchor 800 has a profile similar to that of device 105, as illustrated in FIG. 9. Upon application of a torsional force, anchor 800 screws into the heart wall. In another embodiment, more than one anchor 800 is included such as, for example, an anchor 800 at both proximal end 800A and distal end 800B.

CONCLUSION

The present system includes, among other things, a sensor device such as a pressure monitor. The sensor device is implantable in a heart chamber or elsewhere, and it wirelessly conmmunicates sensor information therefrom. In one embodiment, an implantable pressure monitor provides less invasive chronic measurements of pressure, such as, by way of example, but not by way of limitation, measurements of left ventricular blood pressure. The implantable pressure monitor reduces the risk of obtaining such important measurements, enabling a physician to more accurately diagnose and treat serious heart conditions.

Though particular aspects of the system have been described in conjunction with its use in measuring left ventricular blood pressure, it is understood that the system can also be used for measuring pressure elsewhere. For example, but not by way of limitation, the system can also be used for measuring pressure in other heart chambers, blood vessels (e.g., pulmonary artery), body organs (e.g., the bladder, kidney, uterus), or body cavities (e.g., for intracranial, intraocular, or intrapleural pressure measurements). Moreover, though translumenal implantation has been described using a placement catheter, the present system also includes implantation using an endoscope, laparoscope, or other minimally invasive or other surgical technique. In one example, the implantable sensor device is directed into a urinary bladder via the urethra. In one such embodiment, the implantable sensor device includes a stabilizer or other structure that expands following disposition in the bladder. As a result, the implantable sensor device is retained in the bladder without blocking flow to the urethra.

Though particular aspects of the system have been described in conjunction with its use in measuring pressure, it is understood that the system can also be used with an implantable sensor for sensing manifestations of other physical parameters such as, by way of example, but not by way of limitation, sensing blood gasses or other gasses (e.g., $O_2$, $CO_2$), pH, electrocardiograms, and blood glucose. In another example, the system is used in conjunction with ultrasonic measurements (e.g., measuring blood flow, or measuring heart wall thickness for determining contractility, etc.).

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A medical device implantation method, comprising:
providing an elongate delivery catheter sized for intravascular navigation, the elongate delivery catheter having a distal end portion having a first connector portion;
providing an implantable medical device comprising a pressure sensor device including:
a housing having a second connector portion that is complementary with respect to the first connector portion,
a pressure transducer inside the housing,
a stabilizer mechanically coupled to the housing, the stabilizer operating to connect to tissue when the implantable medical device is moved toward the tissue in a first direction so that the stabilizer engages the tissue, and
a pressure transmission mechanism on the housing for transmitting pressure outside the housing to the pressure transducer;
the implantable medical device being releasably coupled to the distal end portion of the elongate delivery catheter when the first and second connector portions are engaged;
with the first and second connector portions engaged, placing the implantable medical device in a chamber of a patient's heart using the elongate delivery catheter;
connecting the stabilizer with a portion of the heart wall that faces into the heart chamber using the elongate delivery catheter; and
disengaging the first and second connector portions to separate the elongate delivery catheter from the implantable medical device so that the implantable medical device is completely within the heart and the implantable medical device remains affixed to the heart wall with the pressure transmission mechanism located in the heart chamber so as to couple pressure within the heart chamber to the pressure transducer.

2. A method as in claim 1, wherein the implantable medical device is implanted by intravascular insertion.

3. A method as in claim 2, wherein:
the pressure transmission mechanism comprises a pressure transmission catheter having first and second ends, the first end mounted to the housing with the pressure transmission catheter extending to the second end spaced from the housing in a second direction generally opposite the first direction; and
the pressure transmission catheter communicates pressure experienced at the pressure transmission catheter's second end in the heart chamber to the pressure transducer, which generates an electrical signal based on blood pressure in the heart chamber.

4. A method as in claim 1, wherein:
the implantable medical device further includes a wireless communication circuit inside the housing; and
the wireless communication circuit generates a transmission signal based on the signal from the pressure transducer.

5. A method as in claim 1, further comprising using a sheath of the elongate delivery catheter to cover the stabilizer during delivery of the implantable medical device.

6. A method as in claim 1, wherein engaging the stabilizer with a portion of the heart wall comprises using an actuator of the elongate delivery catheter to cause the stabilizer to connect to the patient's heart.

7. A method as in claim 6, wherein the actuator comprises a rotational actuator to connect the stabilizer to the patient's heart by rotation of the implantable medical device that causes the implantable pressure sensor device to move in the first direction.

8. A method as in claim 6, wherein the actuator comprises a push actuator to connect the stabilizer to the patient's heart by pushing the implantable medical device in the first direction.

9. A catheter system, comprising:
an elongate delivery catheter sized for intravascular navigation, the elongate delivery catheter having a distal end portion; and
an implantable medical device comprising a pressure sensor device releasably coupled to the distal end portion of the elongate delivery catheter, the pressure sensor including:
a housing sized for intravascular navigation,
a pressure transducer located in the housing,
a stabilizer adapted for connecting the housing to a heart,
a pressure transmission catheter adapted for receiving the pressure in a heart chamber in which the housing is located, the pressure transmission catheter being coupled to the pressure transducer via a flowable medium to communicate the pressure in the heart chamber to the pressure transducer, and
a wireless communication circuit coupled to the pressure transducer and contained within the housing;
wherein:
the housing defines at least one receptacle and the elongate delivery catheter comprises at a protrusion received in the at least one receptacle;
the implantable medical device is sized for intravascular insertion into the heart;
when the stabilizer connects the housing to the inside surface of a wall of a chamber of the heart, the pressure transmission catheter communicates a blood pressure within the heart chamber to the pressure transducer;
the pressure transducer generates a pressure signal based on the blood pressure in the heart chamber communicated by the pressure transmission catheter;
the wireless communication circuit generates a transmission signal based on the pressure signal from the pressure transducer; and
when the implantable medical device is released from the distal end portion of the elongate delivery catheter, the implantable medical device is completely within the heart.

10. A medical device implantation method, comprising:
providing an elongate delivery catheter sized for intravascular navigation, the elongate delivery catheter having a distal end portion;
providing an implantable pressure sensor device releasably coupled to the distal end portion of the elongate delivery catheter, the implantable pressure sensor device including a housing, a pressure transmission catheter extending from the housing toward the elongate delivery catheter, and a stabilizer, the housing defining at least one receptacle and the elongate delivery catheter comprising at a protrusion received in the at least one receptacle;
placing the implantable pressure sensor device in a chamber of a patient's heart using the elongate delivery catheter;
penetrating tissue of the patient's heart with the stabilizer, the stabilizer for connecting the housing to the patient's heart; and
disengaging the protrusion for the receptacle for releasing the implantable pressure sensor device from the elongate delivery catheter with the pressure transmission catheter extending into the heart chamber.

11. A method as in claim 10, further comprising using a sheath of the elongate delivery catheter to cover the stabilizer during delivery of the implantable pressure sensor device.

12. A method as in claim 10, further comprising using an actuator of the elongate delivery catheter to cause the stabilizer to connect to the patient's heart.

13. A method as in claim 12, wherein the actuator comprises a rotational actuator to connect the stabilizer to the patient's heart by rotation.

14. A method as in claim 12, wherein the actuator comprises a push actuator to connect the stabilizer to the patient's heart by pushing.

15. A method as in claim 10, further comprising using a wireless communication circuit inside the housing to generate a transmission signal based on the pressure sensed by the implantable sensor device.

16. A catheter system, comprising:
- an elongate delivery catheter sized for intravascular navigation, the elongate delivery catheter having a distal end portion having a first connector portion; and
- an implantable medical device comprising a pressure sensor device including:
  - a housing, sized for intravascular navigation, having a second connector portion that is complementary with respect to the first connector portion so as to allow the implantable pressure sensor device to be releasably coupled to the distal end portion of the elongate delivery catheter when the first and second connector portions are engaged;
  - a pressure transducer inside the housing, the pressure transducer operating to generate an electrical signal that represents pressure on the pressure transducer,
  - a stabilizer mechanically coupled to the housing, the stabilizer operating to connect to tissue when the implantable medical device is moved toward the tissue so that the stabilizer engages the tissue surface, and
  - a pressure transmission mechanism on the housing for transmitting pressure outside the housing to the pressure transducer;
  wherein, after the stabilizer engages the tissue surface, the pressure transmission mechanism remains on the same side of the tissue surface as the side that the pressure transmission mechanism was on just before the stabilizer engaged the tissue surface; and
  wherein, when the implantable medical device is released from the distal end portion of the elongate delivery catheter, the implantable medical device is completely localized to the area of the tissue.

17. A catheter system as in claim 16, wherein:
the pressure transmission mechanism comprises a pressure transmission catheter having first and second ends, the first end mounted to the housing with the pressure transmission catheter extending to the second end spaced from the housing:
the pressure transmission catheter communicates pressure experienced at the pressure transmission catheter's second end to the pressure transducer.

18. A catheter system as in claim 16, wherein the pressure transmission mechanism is integrally formed integral with the housing.

19. A catheter system as in claim 16, and further comprising a wireless communication circuit inside the housing wherein the wireless communication circuit generates a transmission signal based on the signal from the pressure transducer.

* * * * *